United States Patent
Banavali et al.

(10) Patent No.: US 7,534,923 B2
(45) Date of Patent: May 19, 2009

(54) METHOD FOR PURIFICATION OF GLYCEROL FROM BIODIESEL PRODUCTION

(75) Inventors: Rajiv Manohar Banavali, Rydal, PA (US); Robert Tryon Hanlon, Philadelphia, PA (US); Alfred Karl Schultz, Maple Glen, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/221,582

(22) Filed: Aug. 5, 2008

(65) Prior Publication Data

US 2009/0048472 A1  Feb. 19, 2009

Related U.S. Application Data

(60) Provisional application No. 60/964,901, filed on Aug. 15, 2007.

(51) Int. Cl.
*C07C 29/74* (2006.01)
*C07C 29/76* (2006.01)
*C07C 29/80* (2006.01)

(52) U.S. Cl. ...................................... 568/869; 568/870

(58) Field of Classification Search .................. 568/869, 568/870
See application file for complete search history.

(56) References Cited

U.S. PATENT DOCUMENTS

| 2,234,400 A | 3/1941 | Evans et al. |
| 2,977,291 A | 3/1961 | Hartmann |
| 2008/0033191 A1 | 2/2008 | Schoerken |
| 2008/0249338 A1 | 10/2008 | Rezkallah |

FOREIGN PATENT DOCUMENTS

GB  1479880  7/1977

OTHER PUBLICATIONS

Miesiac, "Methods for Utlization of the Glycerine Fraction, a Rapeseed Oil Methanolysis By-Product", Przemysl Chemiiczny, vol. 82, pp. 1045-1047 (2003).
Asher, et al., "Glycerol Purification By Ion Exclusion", J. Phys. Chem., vol. 60, pp. 518-521, (1956).

*Primary Examiner*—Elvis O Price
(74) *Attorney, Agent, or Firm*—Kenneth Crimaldi

(57) ABSTRACT

A method for purification of crude glycerol, especially crude glycerol derived from biodiesel production using alkaline catalysts. The method comprises combining the crude glycerol with acid, separating a glycerol layer, and treating the glycerol layer to decolorize it.

9 Claims, No Drawings

METHOD FOR PURIFICATION OF GLYCEROL FROM BIODIESEL PRODUCTION

This application claims the benefit of priority under 35 U.S.C. §119(e) of U.S. Provisional Patent Application No. 60/964,901 filed on Aug. 15, 2007.

BACKGROUND

This invention relates generally to a method for purification of crude glycerol, especially crude glycerol derived from biodiesel production using homogeneous alkaline catalysts.

High fuel prices and environmental concerns are driving development of alternative fuels, especially those derived from renewable resources. One such fuel, commonly known as "biodiesel" fuel, commonly contains methyl esters of fatty acids, and is burned in diesel engines. One source of biodiesel fuel is transesterification of triglycerides, such as vegetable oils with alcohols, typically with methanol and an alkaline catalyst. Glycerol is produced as a byproduct of this process, and typically is contaminated with salts of fatty acids and inorganic salts, including residual alkaline catalysts. The prior art discloses methods purification of glycerol, e.g., in I. Miesiac, Przemysl Chemiczny, vol. 82, pp. 1045-47 (2003). However, poor separation is achieved by prior art methods.

The problem addressed by this invention is to find an improved method for purification of crude glycerol contaminated with residual alkaline catalysts.

STATEMENT OF INVENTION

The present invention is directed to a method for purification of crude glycerol contaminated with alkaline salts. The method comprises steps of: (a) combining the crude glycerol with at least 1 equivalent of sulfuric acid having a concentration of at least 85 wt %; (b) separating a glycerol layer from the salts; and (c) combining said glycerol layer with a solution of sodium borohydride and sodium hydroxide.

DETAILED DESCRIPTION

All percentages are weight percentages ("wt %"), and all temperatures are in ° C., unless otherwise indicated. Weight percentages related to ion exchange resins are based on dry resin. Fatty acids are acyclic aliphatic carboxylic acids containing from 8 to 22 carbon atoms; most commonly, they contain from 12 to 22 carbon atoms. With respect to carbon-carbon bonds, the fatty acids may be saturated, monounsaturated or polyunsaturated (typically 2 or 3 carbon-carbon double bonds).

In addition to glycerol, crude glycerol from biodiesel production using alkaline catalysts typically comprises methanol, water, inorganic salts, salts of fatty acids and fatty acid esters (typically methyl esters, referred to as "FAME"). Salts usually are sodium and/or potassium salts. Levels of fatty acid salts and esters typically are from 5% to 50%. Levels of inorganic salts are from 1% to 5%. These levels typically are expressed together in terms of total cation concentration, which usually is from 0.2% to 5%. In some embodiments of the invention, the total cation concentration is at least 0.5%, alternatively at least 1%. In some embodiments, the total cation concentration is no more than 4%, alternatively no more than 3%. The method of this invention also can be used to purify crude glycerol obtained from other sources, including soap manufacture.

In some embodiments of the invention, the neutralization of crude glycerol with sulfuric acid and the separation are performed in a temperature range from 15° C. to 90° C. In some embodiments of the invention, the temperature is no greater than 80° C., alternatively no greater than 70° C., alternatively no greater than 60° C., alternatively no greater than 50° C. In some embodiments of the invention, the temperature is at least 20° C., alternatively at least 25° C., alternatively at least 30° C.

The concentration and amount of sulfuric acid used in the process affects the separation time and the extent of separation of glycerol from fatty acid methyl esters and salts. In some embodiments of the invention, the sulfuric acid has a concentration of at least 90%, alternatively at least 92%, alternatively at least 94%, alternatively at least 95%, alternatively at least 96%. In some embodiments of the invention, sulfuric acid is added in an amount of at least 1.05 equivalents, based on the amount of base in the crude glycerol, alternatively at least 1.1 equivalents, alternatively at least 1.15 equivalents, alternatively at least 1.2 equivalents. In some embodiments of the invention, the amount of sulfuric acid is no more than 1.5 equivalents, alternatively no more than 1.4 equivalents, alternatively no more than 1.35 equivalents.

In some embodiments of the invention, crude glycerol and sulfuric acid are combined using a static mixer. Neutralization of basic salts in crude glycerol with sulfuric acid results in three layers: (i) an upper layer rich in fatty acids and fatty acid esters; (ii) a middle layer rich in glycerol; and (iii) a bottom layer rich in salts. These layers are separated using standard equipment used for this purpose, e.g., a gravity settler or centrifuge. Preferably, the crude glycerol and sulfuric acid are mixed and then the mixture is passed directly into the separation equipment.

A solution of sodium borohydride and sodium hydroxide is combined with the glycerol layer to neutralize sulfuric acid and reduce colored impurities. In some embodiments of the invention, the solution of sodium borohydride and sodium hydroxide contains at least 5% sodium borohydride, alternatively at least 8%, alternatively at least 10%; the solution preferably contains less than 20% sodium borohydride. In some embodiments of the invention, the solution of sodium borohydride and sodium hydroxide contains at least 20% sodium hydroxide, alternatively at least 30%, alternatively at least 35%; preferably the solution contains less than 45% sodium hydroxide. An example of a suitable solution is sold by Rohm and Haas Company under the trade name BOROL solution, which contains about 12% sodium borohydride and about 40% sodium hydroxide. In some embodiments of the invention, the amount of solution combined with 100 g of the glycerol layer is from 0.7 g to 1.5 g, alternatively from 0.75 g to 1.3 g, alternatively from 0.8 g to 1.2 g. In some embodiments of the invention, the temperature during treatment of the glycerol layer with the solution is in a range from 15° C. to 90° C. In some embodiments of the invention, the temperature is no greater than 80° C., alternatively no greater than 70° C., alternatively no greater than 60° C., alternatively no greater than 50° C. In some embodiments of the invention, the temperature is at least 20° C., alternatively at least 25° C., alternatively at least 30° C. In some embodiments of the invention, the contact time between the glycerol layer and the solution is at least 10 minutes. Much longer times are not believed to be detrimental to the process, but preferably, the treatment time is no longer than 24 hours.

Optionally, the glycerol layer is further treated to remove salts, using ion exclusion chromatography, as disclosed in pending European application Ser. No. 07290412.1, filed Apr. 4, 2007. Residual water and methanol can be removed via standard evaporation techniques, and borate salts and other solids removed by filtration.

Optionally, the upper layer, which typically contains fatty acid esters, fatty acids and glycerides, can be recycled to a biodiesel process.

EXAMPLES

Example 1

Separation of Glycerin using Stoichiometric 96% $H_2SO_4$

Crude glycerin from a biodiesel process (commercial sample; 0.926 meq base/gram sample) was added to a round bottomed flask. A stoichiometric amount of 96% sulfuric acid was added, and the reaction mixture was stirred at 400 rpm for 30 mins. The temperature of the mixture rose from room temperature to 65° C. upon addition of the acid. The mixture was transferred to a separatory funnel and allowed to separate. After standing for requisite time, the material separated into 3 distinct layers; top-methyl ester, middle-glycerin, bottom-salts. Time to separation (efficiency) and analysis of layers (effectiveness) are summarized in table 1.

Example 2

Separation of Glycerin using Excess 96% $H_2SO_4$

Crude glycerin (commercial sample; 0.926 meq base/gram sample) was added to a round bottomed flask. A 25% molar excess of 96% sulfuric acid was added, and the reaction mixture was stirred at 400 rpm for 30 mins. The mixture was transferred to a separatory funnel and allowed to separate. After standing for requisite time, the material separated into 3 distinct layers; top-methyl ester, middle-glycerin, bottom-salts. Time to separation (efficiency) and analysis of layers (effectiveness) are summarized in table 1.

Example 3

Separation of Glycerin using Stoichiometric 70% $H_2SO_4$

Crude glycerin (commercial sample; 0.926 meq base/gram sample) was added to a round bottomed flask. A stoichiometric amount of 70% sulfuric acid (diluted in water) was added, and the reaction mixture was stirred at 400 rpm for 30 mins. The mixture was transferred to a separatory funnel and allowed to separate. After standing for requisite time, the material separated into 3 distinct layers; top-methyl ester, middle-glycerin, bottom-salts. Time to separation (efficiency) and analysis of layers (effectiveness) are summarized in table 1.

Example 4

Separation of Glycerin using Excess 70% $H_2SO_4$

Crude glycerin (commercial sample; 0.926 meq base/gram sample) was added to a round bottomed flask. A 25% molar excess of 70% sulfuric acid (diluted in water) was added, and the reaction mixture was stirred at 400 rpm for 30 mins. The mixture was transferred to a separatory funnel and allowed to separate. After standing for requisite time, the material separated into 3 distinct layers; top-methyl ester, middle-glycerin, bottom-salts. Time to separation (efficiency) and analysis of layers (effectiveness) are summarized in table 1.

| [$H_2SO_4$] (diluted in water) | Stoichiometry Acid/base | *Efficiency (mins. to separation) | ‡Effectiveness FAME (% top/ % middle) | ‡Effectiveness Glycerin (% middle/ % top) |
|---|---|---|---|---|
| 96% | 0.75 | >15:00 | ND | ND |
| 96% | 1.00 | 4:45 | 17.5 | 6.33 |
| 96% | 1.25 | 2:00 | 27.6 | 49.5 |
| 70% | 0.75 | >15:00 | ND | ND |
| 70% | 1.00 | 8:25 | 11.9 | 4.55 |
| 70% | 1.25 | 3:00 | 17.9 | 11.5 |

*Separation efficiency determined by time needed for layers to separate, faster separation, more efficient method.
‡Separation effectiveness determined by ratio % FAME in upper layer divided by % FAME in middle layer and by ratio of % glycerin (free and total glycerin) in middle layer divided by % glycerin in top layer

Example 5

Sodium Borohydride Treatment of Resultant Glycerin from Ex. 2

The glycerin layer (Gardner color 4) obtained from example 2 is treated with 12% $NaBH_4$ (in 40% caustic solution) to pH 8-9. This reaction mixture is stirred at room temperature for 15 minutes and filtered to remove solid salts. The color and purity of the final material are expected to be <1 Gardner, and > 98% glycerin. The dissolved salts generated by the sodium borohydride treatment are removed by ion-exclusion chromatography.

The invention claimed is:

1. A method for purification of crude glycerol contaminated with alkaline salts; said method comprising steps of:
    (a) combining the crude glycerol with at least 1 equivalent of sulfuric acid having a concentration of at least 85 wt %;
    (b) separating a glycerol layer from the salts; and
    (c) combining said glycerol layer with a solution of sodium borohydride and sodium hydroxide.

2. The method of claim 1 in which the crude glycerol comprises fatty acid methyl esters.

3. The method of claim 2 in which the sulfuric acid has a concentration of at least 90 wt %.

4. The method of claim 3 in which at least 1.1 equivalents of sulfuric acid are combined with the crude glycerol.

5. The method of claim 4 in which the solution of sodium borohydride and sodium hydroxide contains 8-20 wt % sodium borohydride and 35-45 wt % sodium hydroxide.

6. The method of claim 5 in which the crude glycerol is a byproduct of biodiesel production.

7. The method of claim 6 in which the solution of sodium borohydride and sodium hydroxide is added in an amount from 0.7 g to 1.5 g per 100 g of glycerol layer.

8. The method of claim 7 in which the sulfuric acid has a concentration of at least 94 wt %.

9. The method of claim 8 in which at least 1.15 equivalents of sulfuric acid are combined with the crude glycerol.

* * * * *